United States Patent
Brown et al.

(10) Patent No.: US 6,750,227 B2
(45) Date of Patent: Jun. 15, 2004

(54) METHOD OF TREATMENT OF NEUROPSYCHIATRIC SYMPTOMS IN PATIENTS WITH ALZHEIMER'S DISEASE

(75) Inventors: Frank Brown, Steeple Bumpstead (GB); James P. Mc Cafferty, Shamong, NJ (US); Eve Naomi Cedar, London (GB)

(73) Assignees: SmithKline Beecham Corporation, Philadelphia, PA (US); SimthKline Beecham p.l.c., Brentford (GB)

( * ) Notice: Subject to any disclaimer, the term of this patent is extended or adjusted under 35 U.S.C. 154(b) by 0 days.

(21) Appl. No.: 10/372,577

(22) Filed: Feb. 21, 2003

(65) Prior Publication Data

US 2003/0125353 A1 Jul. 3, 2003

Related U.S. Application Data

(63) Continuation of application No. 10/124,707, filed on Apr. 17, 2002, now abandoned, which is a continuation of application No. 09/951,659, filed on Sep. 13, 2001, now abandoned, which is a continuation of application No. 09/740,628, filed on Dec. 19, 2000, now abandoned, which is a continuation of application No. 09/557,954, filed on Apr. 24, 2000, now abandoned, which is a continuation of application No. 09/354,041, filed on Jul. 15, 1999, now abandoned.

(30) Foreign Application Priority Data

Jul. 15, 1998 (GB) .............................. 9815383

(51) Int. Cl.$^7$ ............................... A61K 31/46
(52) U.S. Cl. ...................................... 514/305
(58) Field of Search ........................ 514/305

(56) References Cited

U.S. PATENT DOCUMENTS 6,284,771 B1   9/2001   Mitch et al. ............... 514/305

FOREIGN PATENT DOCUMENTS

| WO | 98/04258 | * | 2/1998 |
| WO | 98/46226 |   | 10/1998 |

OTHER PUBLICATIONS

Loudon et al., Journal of Pharmacology & Experimental Therapeutics, 283(3), 1059–68 (Dec., 1997).*
Bromidge et al., J. Med. Chem., 40(26), 4265–4280 (1997).*
Harries et al., British Journal of Pharmacology, 124(2), 409–415 (1998).*
Dr. Simon B.N. Thompson, "Dementia A Guide for Health Care Professionals", (1998), Table of Contents and pp. 15–36.

* cited by examiner

Primary Examiner—Phyllis G. Spivack
(74) Attorney, Agent, or Firm—Linda E. Hall; Stephen Venetianer; Charles M. Kinzig

(57) ABSTRACT

The use of [R-(Z)]-α-(methoxyimino)-α-(1-azabicyclo[2.2.2]oct-3-yl)acetonitrile or a pharmaceutically acceptable salt thereof for the treatment of neuropsychiatric symptoms in patients with Alzheimer's Disease is disclosed.

2 Claims, No Drawings

METHOD OF TREATMENT OF NEUROPSYCHIATRIC SYMPTOMS IN PATIENTS WITH ALZHEIMER'S DISEASE

This is a continuation of application Ser. No 10/124,707, filed Apr. 17, 2002 now abandoned; which is a continuation of application Ser. No. 09/951,659 filed Sep. 13, 2001, now abandoned; which is a continuation of Ser. No. 09/740,628 filed Dec. 19, 2000, now abandoned; which is a continuation of Ser. No. 09/557,954 filed Apr. 24, 2000, now abandoned; which is a continuation of Ser. No. 09/354,041 filed Jul. 15, 1999, now abandoned; which claims priority from GB application GB 9815383.6 filed Jul. 15, 1998.

This invention relates to a method for the treatment of psychosis and neuropsychiatric symptoms and to a compound for use in such method.

EP-A-0392803 (Beecham Group p.l.c.) discloses certain azabicyclic compounds which enhance acetylcholine function via an action at muscarinic receptors within the central nervous system, including [R-(Z)]-α-(methoxyimino)-α-(1-azabicyclo[2.2.2]oct-3-yl)acetonitrile (Compound (I)), and pharmaceutically acceptable salts, their use in the treatment and/or prophylaxis of dementia and processes by which such compounds may be made.

WO-93/17018 and WO-95/31456 disclose alternative processes by which Compound (I) may be made.

It has now been found that Compound (I) is of potential use in the treatment of psychosis and neuropsychiatric symptoms, and is of particular use in the treatment of the symptoms of psychosis such as delusions, hallucinations and agitation and neuropsychiatric symptoms such as anxiety, depression, apathy, elation, disinhibition, irritability and wandering in patients with Alzheimer's Disease, more particularly in such patients with severe behavioural disturbance as categorised by baseline scores on the NeuroPsychiatric Inventory (NPI) assessment scale (baseline NPI>20=severe).

According to the present invention, there is provided the use of Compound (I) or a pharmaceutically acceptable salt thereof in the manufacture of a medicament for the treatment of psychosis or other neuropsychiatric symptoms.

In a further aspect the invention provides a method for the treatment of psychosis or other neuropsychiatric symptoms comprising administering to the patient an effective, non-toxic amount of Compound (I) or a pharmaceutically acceptable salt thereof.

Compound (I) can form acid addition salts with strong acids. The term pharmaceutically acceptable salt encompasses solvates and hydrates.

Compound (I) is preferably provided in a pharmaceutical composition, which comprises Compound (I) or a pharmaceutically acceptable salt thereof, and a pharmaceutically acceptable carrier. The invention thus further provides a pharmaceutical composition, which comprises Compound (I) or a pharmaceutically acceptable salt thereof for use in the treatment of psychosis or other neuropsychiatric symptoms.

In a preferred aspect Compound (I) is provided in the form of the monohydrochloride.

The composition may be in the form of tablets, capsules, powders, granules, lozenges, suppositories, reconstitutable powders, or liquid preparations such as oral or sterile parenteral solutions or suspensions.

In order to obtain consistency of administration it is preferred that a composition is in the form of a unit dose.

Unit dose presentation forms for oral administration may be tablets and capsules and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate; disintegrants, for example starch, polyvinylpyrrolidone, sodium starch glycollate or microcrystalline cellulose; or pharmaceutically acceptable wetting agents such as sodium lauryl sulphate.

Solid oral compositions may be prepared by conventional methods of blending, filling, tabletting or the like. Repeated blending operations may be used to distribute the active agent throughout those compositions employing large quantities of fillers. Such operations are of course conventional in the art. The tablets may be coated according to methods well known in normal pharmaceutical practice, in particular with an enteric coating.

Oral liquid preparations may be in the form of, for example, emulsions, syrups, or elixirs, or may be presented as a dry product for reconstitution with water or other suitable vehicle before use. Such liquid preparations may contain conventional additives such as suspending agents, for example sorbitol, syrup, methyl cellulose, gelatin, hydroxyethylcellulose, carboxymethylcellulose, aluminium stearate gel, or hydrogenated edible fats; emulsifying agents, for example lecithin, sorbitan monooleate, or acacia; non-aqueous vehicles (which may include edible oils), for example almond oil, fractionated coconut oil, oily esters such as esters of glycerine, propylene glycol, or ethyl alcohol, preservatives, for example methyl or propyl p-hydroxybenzoate or sorbic acid; and if desired conventional flavouring or colouring agents.

For parenteral administration, fluid unit dosage forms are prepared utilizing the compound and a sterile vehicle, and, depending on the concentration used, can be either suspended or dissolved in the vehicle. In preparing solutions the compound can be dissolved in water for injection and filter sterilized before filling into a suitable vial or ampoule and sealing. Advantageously, adjuvants such as a local anaesthetic, a preservative and buffering agents can be dissolved in the vehicle. To enhance the stability, the composition can be frozen after filling into the vial and the water removed under vacuum. Parenteral suspensions are prepared in substantially the same manner, except that the compound is suspended in the vehicle instead of being dissolved, and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

The composition may contain from 0.1% to 99% by weight, preferably from 10–60% by weight, of the active material, depending on the method of administration.

The invention additionally provides a pharmaceutical composition as above defined for use in the treatment of psychosis.

The dose of the compound will vary in the usual way with the seriousness of the disorder, the weight of the sufferer, and the relative efficacy of the compound. However, as a general guide suitable daily doses below 0.01 mg/kg more particularly 0.003 mg/kg and below, for example 0.0001–0.003 mg/kg, such as 0.00035–0.003 mg/kg, 0.0007–0.003 mg/kg, 0.0001–0.0007 mg/kg or 0.00035–0.002 mg/kg. Suitable unit doses to achieve such daily doses are 5, 12.5, 25, 50 or 75 µg, administered twice daily and, in the case of 50 µg, once daily and such therapy may well extend for a number of years.

Within the above indicated dosage ranges no unacceptable toxicological effects are indicated for Compound (I).

The following pharmacological data illustrates the invention.

Biological Data

Amphetamine Induced Hyperactivity and Catalepsy in the Rat

Materials

Male Sprague Dawley rats from Charles River UK Ltd were used in all experiments. The rats were allowed to acclimatise to their housing conditions (12 h light/dark cycle with ad lib food and water: 6 rats per cage) for at least 5 days before experiments. On the day of use, rats weighed 220–340 g.

Dexamphetamine sulphate (Lot No. 33HS44) was obtained from Sigma Chemical Co. UK. and dissolved in 0.9% w/v saline. Haloperidol (Lot No. 37F-00123) was obtained from Sigma Chemical Co. UK. and dissolved with an equal weight of (+)-tartaric acid in water.

[R-(Z)]-α-(methoxyimino)-α-(1-azabicyclo[2.2.2]oct-3-yl)acetonitrile monohydrochloride (Compound (I)) is described in EP-A-0392803 as the oxalate salt. Compound (I) was dissolved in 0.9% w/v saline. All drug doses refer to the base equivalent.

Methods

1. Amphetamine-Induced Hyperactivity

Rat locomotor activity was measured in 2 racks of "AM logger" AM 1052 activity monitors (Linton Instrumentation). Each rack held 8 individual perspex boxes (42 cm×21 cm×21 cm) containing a thin bed of sawdust. For each box, 8 infra red light beams traversed the short axis and 4 infra red light beams traversed the long axis. The light beams were focussed on to photoelectric cells. Each rack of monitors was controlled by a 386 microcomputer using AMLOGGER "Activity Monitor Data Logger Version 4.02" software.

Rats (n=8 per treatment group) were weighed and injected with saline or test drug in a volume of 2 ml/kg po. and then placed in the locomotor activity boxes for a period of habituation. After 25–30 minutes, the rats were injected with saline (1 ml/kg sc) or dexamphetamine sulphate (0.4 mg/kg) and then returned to the locomotor activity boxes. Locomotor activity was then monitored for a further 60 minutes in 5 min blocks. After discarding the first 5 minute block so as to minimise handling artefacts, the total beam break tally for the final 55 min. was subjected to $\log_{10}$ transformation before being analysed by 1 factor analysis of variance and Dunnett's t-test for multiple comparisons. ED50 with 95% confidence intervals were calculated from the log10 transformed data using a statistical package (GETED50CI) in RSE (Bolt, Beranek and Newman Inc, 1992).

2. Catalepsy

For catalepsy experiments, rats (n=6 per treatment group) were weighed and injected with saline or test drug in a volume of 2 ml/kg po., and then returned to their home cages. Haloperidol was included in the experiment as a positive control. At 30, 60 and 90 minutes post dose, the rats were positioned so that their hind-legs contacted the bench surface, and their fore-legs were located over the horizontal bar. A maximum measurement time of 120 sec. was used, after which, if the rats were still on the bar, they were returned to their home cages. A rat was considered to be cataleptic if it remained on the bar for at least 30 sec. at the 90 min. time point. Data was analysed by logistic regression analysis in SAS-RA (Version 2.1) (SAS Institute Inc., Cary, N.C., USA).

Results

In the amphetamine-induced hyperactivity model, a standard behavioural test which is predictive of antipsychotic efficacy, Compound (I) (0.01–0.3 mg/kg po; 30 min pretreatment) caused a dose related reversal of amphetamine-induced hyperactivity in the rat which reached significance (P<0.01) at a dose of 0.3 mg/kg. The $ED_{50}$ for this inhibitory effect was 0.25 mg/kg (95% CI=0.14–0.75). Activity in this model indicates utility in the treatment of psychosis.

Conversely, in the above catalepsy test predictive of neuroleptic-induced extrapyramidal side-effects, Compound (I) did not produce catalepsy when tested 90 min after dosing in the rat at doses up to 0.3 mg/kg po, wheras haloperidol produced catalepsy in 6 of 6 rats at 2.8 mg/kg.

The data suggest that Compound (I) may possess behaviour modifying effects consistent with antipsychotic activity at doses which would not produce extrapyramidal side-effects, indicating potential use in the treatment of psychosis.

Clinical Data (Retrospective Analysis)

Compound (I) has been assessed in clinical trials of Alzheimer's disease. In addition to investigating the effects on cognition and global functioning, scales to assess effects of Compound (I) on behavioural symptoms commonly found in Alzheimer patients (which include delusions, hallucinations, agitation, anxiety, depression, apathy, elation, disinhibition, irritability and wandering) were prospectively included in two of the trials. The prospectively defined analysis of these studies indicated a positive effect of Compound (I) on behaviour.

A retrospective meta-analysis on the combined data was then conducted and effects on individual symptoms assessed. Results are shown in Table 1 (a negative score denotes an improvement and a positive score denotes a deterioration).

TABLE 1

All Patients (NB: Statistical analyses were not conducted on the individual symptoms)

| Parameter/ Dose | Placebo | 25 µg bid | *p value (Active vs placebo) | 50 µg uid | *p value (Active vs placebo) |
| --- | --- | --- | --- | --- | --- |
| Total NPI | +2.5 | +0.7 | 0.064 | +0.3 | 0.026 |
| Agitation | −0.2 | −0.5 | | −0.6 | |
| Apathy | −0.7 | −1.1 | | −1.5 | |
| Depression | −0.3 | −0.3 | | −0.6 | |
| Delusions | −0.9 | −0.7 | | −0.6 | |
| Hallucinations | 0 | −1.5 | | −0.7 | |
| Wandering | −0.7 | −1.2 | | −1.0 | |
| Anxiety | −0.8 | −0.9 | | −1.5 | |
| Elation | 0.1 | −1.1 | | −1.9 | |
| Disinhibition | 0 | −0.7 | | −0.7 | |
| Irritability | −0.6 | −0.4 | | −0.9 | |

*No adjustment has been made for multiple comparisons

Country adjusted differences were calculated as the difference between the adjusted least square means; allowing estimates from each country to be combined in a manner whereby the most precise estimate is given more weight.

This analysis showed a statistically significant improvement following treatment with Compound (I) 50 µg uid compared with placebo, on the NPI total score (country adjusted difference: −2.1; p=0.026; 95% confidence interval: −4.1, −0.3). The analysis of the difference between Compound (I) 25 kg bid and placebo was in favour of Compound (I) but failed to achieve statistical significance (country adjusted difference: −1.8; p=0.064; 95% confidence interval −3.8, 0.1). Improvements were also seen in individual symptoms, for example in psychotic symptoms (hallucinations, agitation) and other neuropsychiatric symptoms often observed in Alzheimer's disease.

Following this analysis, a further retrospective analysis was conducted on the subgroup of patients who presented with severe behavioural disturbance at the start of the study (defined as a baseline NPI score>20). Country adjusted differences were calculated as the difference between the adjusted least square means; allowing estimates from each country to be combined in a manner whereby the most precise estimate is given more weight. In this subgroup, the effects of Compound (I) on behaviour were even more marked (see Table 2). Thus, a statistically and clinically significant improvement was seen in total NPI score compared with placebo at both 25 µg bid (country adjusted difference: −7.18; p=0.043; 95% confidence interval: −14.1, −0.2) and 50 µg uid (country adjusted difference: −7.86; p=0.019; 95% confidence interval: −14.4, −1.3) and marked improvements were also seen on individual symptoms, for example in psychotic symptoms (hallucinations, agitation) and other neuropsychiatric symptoms often observed in Alzheimer's disease, for example apathy, anxiety, disinhibition and wandering

TABLE 2

Endpoint Scores: Change from baseline
(Patients with baseline NPI >20)
(NB: Statistical analyses were not conducted on the individual symptoms)

| Parameter/<br>Dose | Placebo | 25 µg<br>bid | *p value<br>(Active vs<br>Placebo) | 50 µg<br>uid | *p value<br>(Active vs<br>Placebo) |
|---|---|---|---|---|---|
| Total NPI | +1.7 | −4.0 | 0.043 | −6.1 | 0.019 |
| Agitation | −0.1 | 0 | | −0.6 | |
| Apathy | −0.1 | −1.4 | | −1.6 | |
| Depression | −0.7 | 0 | | −1.1 | |
| Delusions | −1.3 | −0.8 | | −1.4 | |
| Hallucinations | −0.4 | −2.1 | | −1.4 | |
| Wandering | −0.2 | −1.7 | | −1.3 | |
| Anxiety | −0.5 | −1.9 | | −1.8 | |
| Elation | +0.6 | −1.7 | | −2.5 | |
| Disinhibition | +0.4 | −0.8 | | −1.1 | |
| Irritability | −0.9 | −0.7 | | −1.2 | |

*No adjustment has been made for multiple comparisons

These results suggest that Compound (I) may have efficacy in the treatment of psychosis in Alzheimer's disease, more particularly in patients with severe behavioural disturbance and also in the treatment of other neuropsychiatric behaviours commonly observed in patients suffering from AD. more particularly those with severe behavioural disturbance.

What is claimed is:

1. A method for the treatment of neuropsychiatric symptoms in patients with Alzheimer's Disease with severe behavioral disturbance wherein the symptoms are selected from the group consisting of agitation, apathy, depression, delusions, hallucinations, wandering, anxiety, elation, disinhibition and irritability, comprising administering to the patient an effective, non-toxic amount of [R-(Z)]-α-(methoxyimino)-α-(1-azabicyclo[2.2.2]oct-3-yl)acetonitrile or a pharmaceutically acceptable salt thereof.

2. A method according to claim 1 wherein the pharmaceutically acceptable salt is the monohydrochloride.

* * * * *